(12) United States Patent
Hansen et al.

(10) Patent No.: US 7,207,976 B2
(45) Date of Patent: Apr. 24, 2007

(54) INJECTION DEVICES

(75) Inventors: Nick Hansen, Oxford (GB); Mark Eaton, Oxon (GB)

(73) Assignee: Owen Mumford Limited, Oxford (GB)

( * ) Notice: Subject to any disclaimer, the term of this patent is extended or adjusted under 35 U.S.C. 154(b) by 173 days.

(21) Appl. No.: 10/492,425

(22) PCT Filed: Oct. 9, 2002

(86) PCT No.: PCT/GB02/04573

§ 371 (c)(1),
(2), (4) Date: Apr. 12, 2004

(87) PCT Pub. No.: WO03/030972

PCT Pub. Date: Apr. 17, 2003

(65) Prior Publication Data

US 2004/0243072 A1  Dec. 2, 2004

(30) Foreign Application Priority Data

Oct. 10, 2001 (GB) ................................. 0124297.3

(51) Int. Cl.
*A61M 5/00* (2006.01)
*B65D 83/10* (2006.01)

(52) U.S. Cl. ...................................... 604/263; 206/365
(58) Field of Classification Search .......... 604/164.08, 604/192, 197, 263; 215/200, 201, 207–209, 215/213, 216–221, 223–225, 316–317, 321; 206/365–366
See application file for complete search history.

(56) References Cited

U.S. PATENT DOCUMENTS 4,598,833 A * 7/1986 Herr ............................ 215/220
5,968,021 A   10/1999 Ejlersen

* cited by examiner

*Primary Examiner*—Catherine S. Williams
(74) *Attorney, Agent, or Firm*—Young & Thompson

(57) ABSTRACT

A cap (16) is provided for the type of injection device (1) which presents a needle assembly (11) to the exterior thereof for removal after use. The cap is of two part construction with a shell (17) of hard material, having opposite inwardly flexible tongues (19) defined by slots in the shell, and an over-mould (18) of relatively soft deformable material, extending over at least the tongues and the slots. The tongues are squeezable towards each other through the over-mould to grip the needle assembly when the cap is fitted after an injection, thus enabling the needle assembly to be removed with the cap so that the user does not come into contact with the used needle.

19 Claims, 3 Drawing Sheets

INJECTION DEVICES

BACKGROUND OF THE INVENTION

This invention concerns injection devices for medical use and in particular caps for such devices.

DESCRIPTION OF THE RELATED ART

After use, the needle of a syringe has to be safely disposed of. In many injection devices the forward end of the syringe is left exposed so that the user can remove the needle assembly, leaving the capsule of the syringe in place. It is not generally practical or recommended to replace the plastic sheath which initially covers the needle. The tip of the needle can easily pierce the plastic. So the needle assembly has to be unscrewed or pulled off with the needle tip exposed, and this represents a danger.

However, most injection devices have a cap which fits to the forward end of the barrel that houses the syringe, this cap providing mechanical protection of the syringe housing. The cap is removed immediately prior to injection.

SUMMARY OF THE INVENTION

It is the aim of this invention to use the cap to remove the needle assembly safely after use.

According to the present invention there is provided a cap for an injection device of the type which presents a needle assembly to the exterior thereof for removal after use, the cap being of two part construction with a shell of hard material having opposite inwardly flexible tongues defined by slots in the shell and an over-mould of relatively soft deformable material extending over at least the tongues and the slots, the tongues being squeezable towards each other through the over-mould to grip the needle assembly when the cap is fitted after an injection.

With the needle assembly so gripped, the cap can be removed, for example by unscrewing, and the needle assembly will come with it. That assembly can then be dropped into a sharps bin by relaxing the grip, and the user need never touch it.

The cap will generally be elongate, closed at one end and open at the other. The tongues may be defined by generally U-shaped slots, the base of each U being positioned away from the closed end of the cap.

The cap may be coned, narrowing towards its closed, forward end and then the arms of each U may converge towards each other so that the tongues widen towards the open end, following the shape of the cap.

Preferably, the tongues will be thinner, over substantial part of their area, than the rest of the shell to facilitate flexure.

The over-mould need not conceal the whole shell, and it may be mainly over just the tongues and slots, with its outer surface flush with the exposed parts of the shell.

Conveniently, the over-mould will be of rubber, with depressions forming finger grips over the ends of the tongues which are to be pressed inwards. The over-mould may have a positive interlock with the shell, for example by inwardly projecting ribs engaging in slots in the shell. These may be adjacent the open end of the cap.

BRIEF DESCRIPTION OF THE DRAWINGS

For a better understanding of the invention one embodiment will now be described, by way of example, with reference to the accompanying drawings, in which.

DESCRIPTION OF THE PREFERRED EMBODIMENTS

Figure 1:
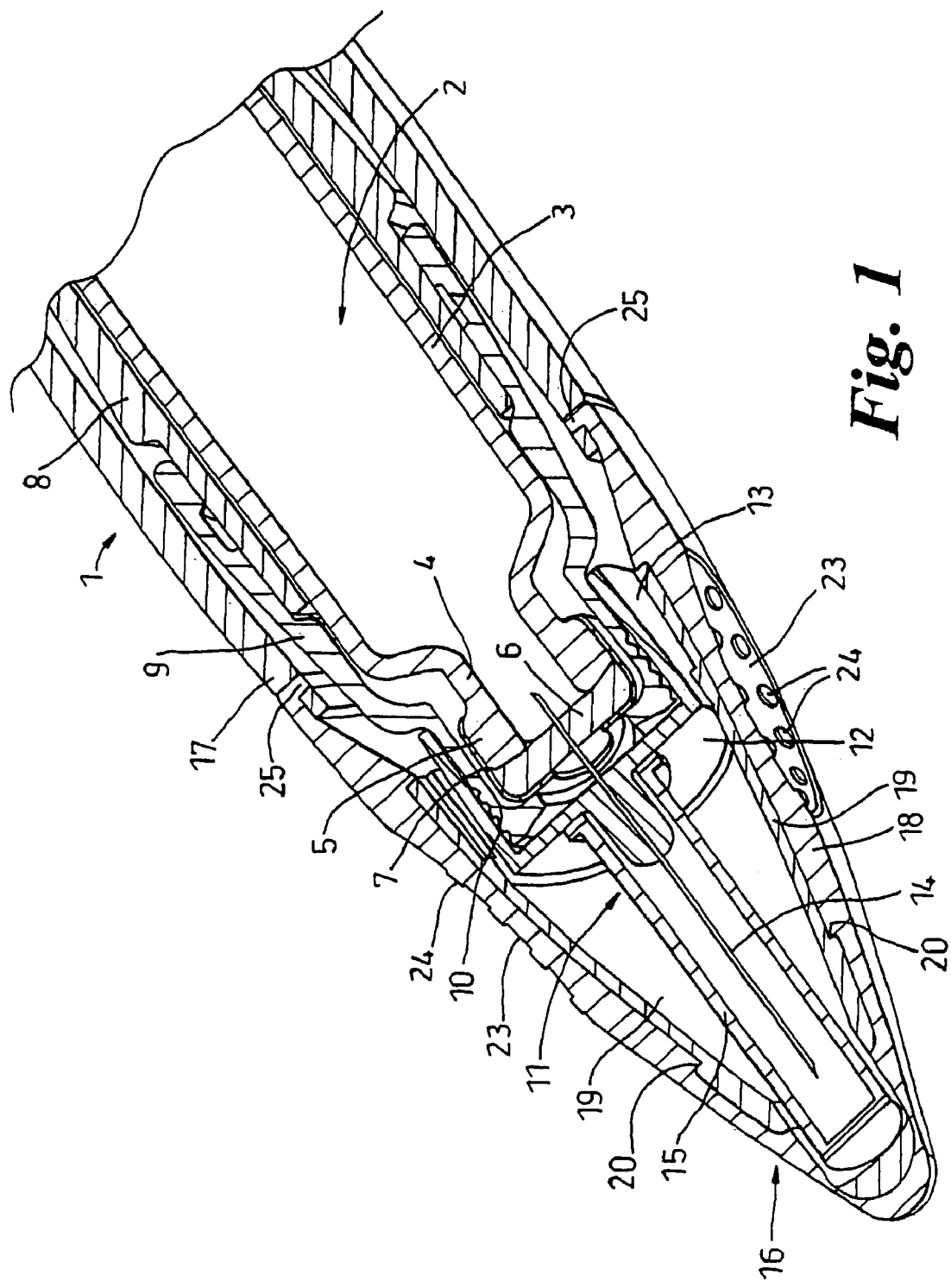
FIG. 1 is a cut-away perspective view of the leading end of an injection device with a cap fully fitted.
Figure 2:
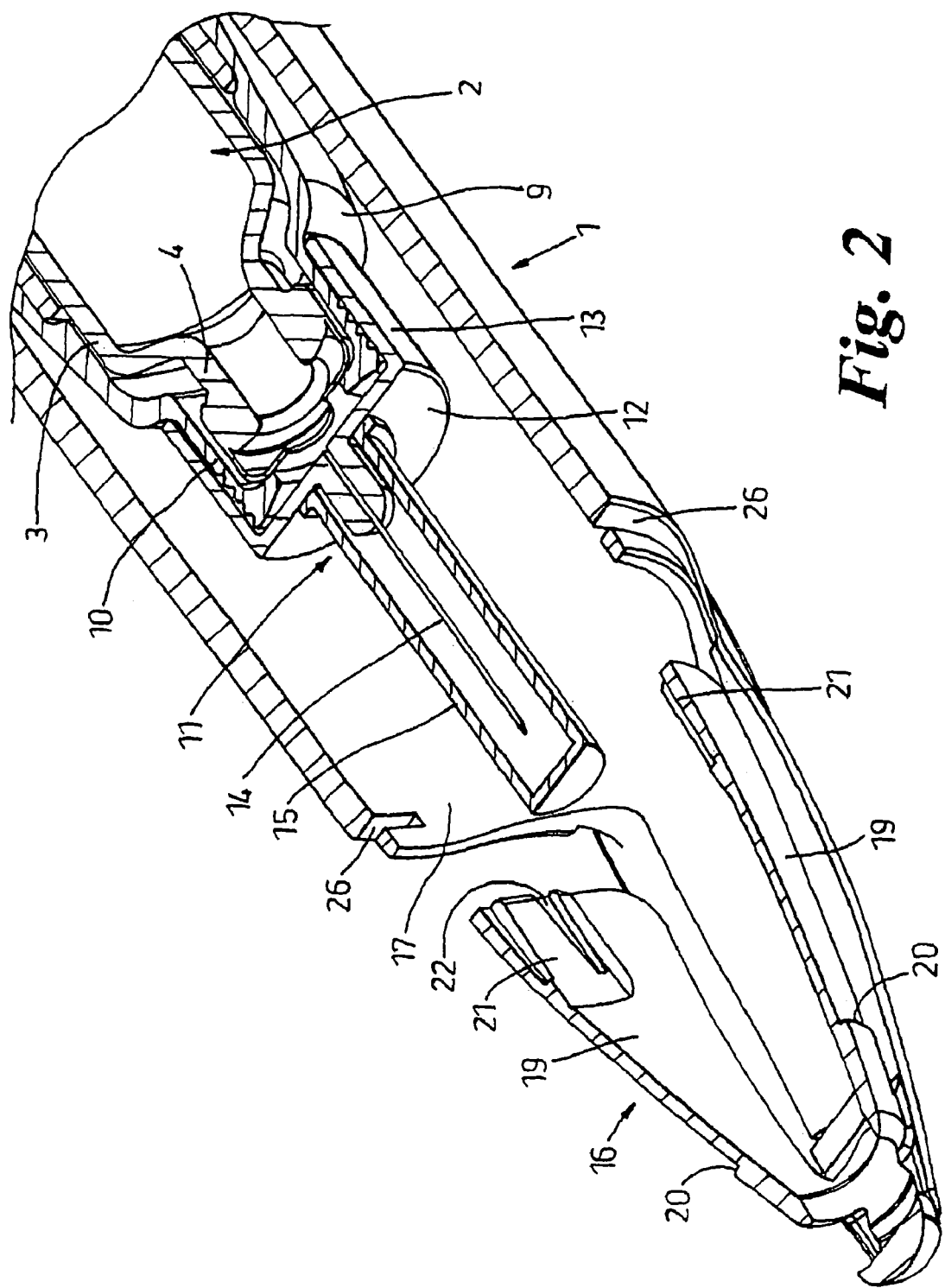
FIG. 2 is a similar view of the device with the cap particularly withdrawn and with a part thereof removed.
Figure 3:
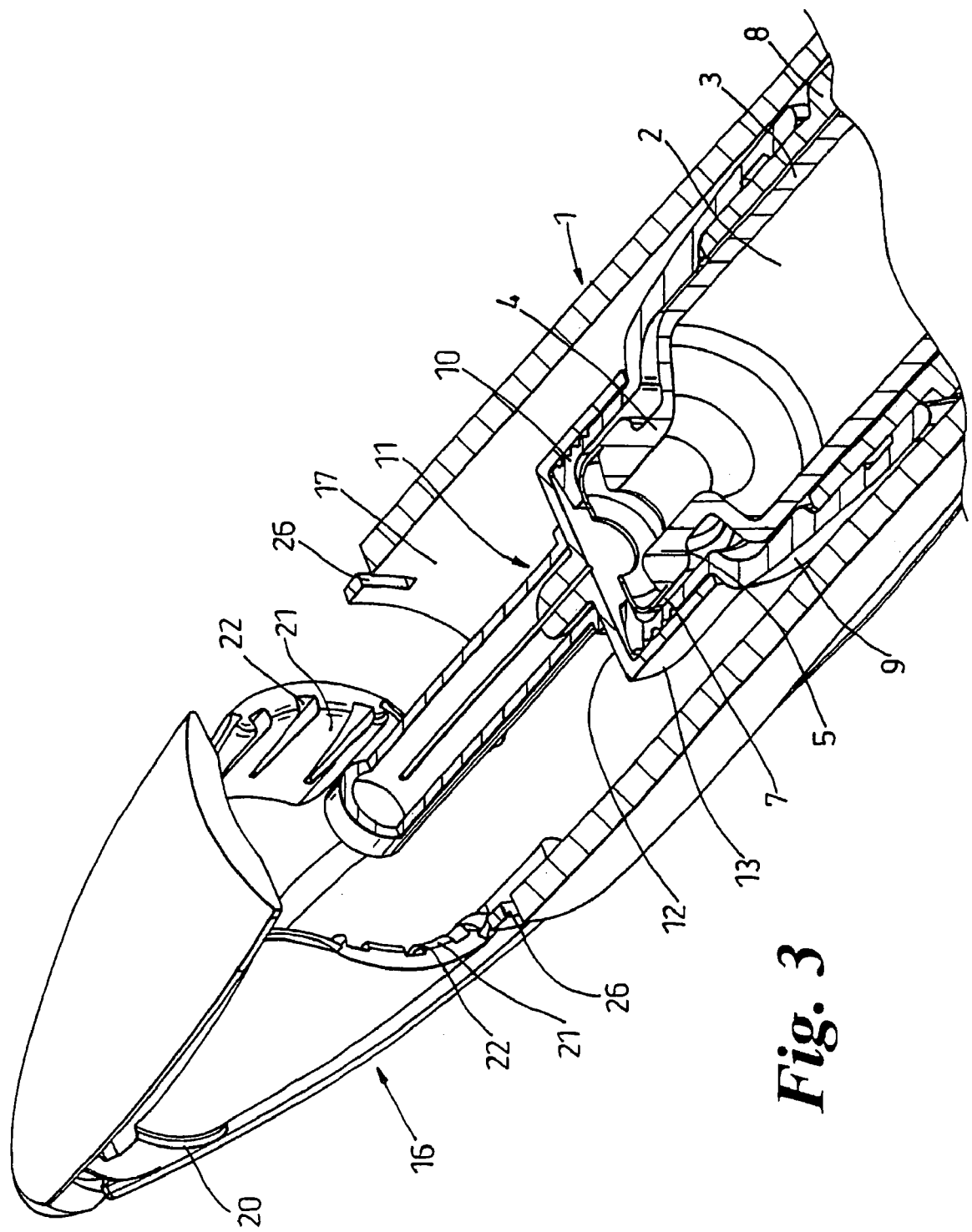
FIG. 3 is another cut-away perspective view of the device from a different angle, with the cap particularly withdrawn and with a part thereof removed.

The injection device 1 houses a syringe 2 of conventional form. It has a capsule 3 narrowing to a neck 4 at its leading end where it terminates in a head 5 with a membrane 6 captive by a metal band 7. The syringe 2 is entered into a two-part barrel comprising a main sleeve 8 containing most of the capsule 3 and a leading part 9 which shrouds the forward end of the syringe. The part 9 reduces to an externally screwed threaded portion 10 closely embracing the head 5. This portion 10 receives a needle assembly 11 comprising a cup-like element 12 which has a rearwardly extending skirt 13 internally screw threaded to mate with the portion 10. A double-ended needle 14 extends co-axially through the thickened base of the cup, and when the needle assembly 11 is screwed on to the syringe carrier the rear end of the needle 14 punctures the membrane 6. Before an injection, the forward end of the needle 14 is covered by a sheath 15.

This far, the arrangement is generally conventional.

Except when the device is actually being used the needle must be protected by more than the sheath 15, and so the barrel has a cap 16 which fits to its leading end. This is of a two-part construction comprising a hard plastics shell 17 and a rubber over-mould 18 shown only in FIG. 1. The shell is of a cone-like form but is cut-away to create two diametrically opposed tongues 19 which join to the shell 17 near the tip of the cone and which widen as they extend rearwardly. Externally the tongues step inwards at shoulders 20 near their narrow ends so that they are mostly thinner than the rest of the shell. But at their rear ends they have internal wedge-like formations 21 which thicken towards the rear and which have axially parallel grooves 22. The nature of the plastics material from which the shell 17 is moulded is such that the tongues 19 can flex inwardly about their leading ends.

The rubber over-mould 18 extends over these tongues 19 and the slots by which they are defined. Externally, it is flush with the exposed parts of the shell 17 but in the region of the formations 21 the over-mould has shallow depressions 23 with studs 24. To the rear of these the over-mould thins and then terminates at inwardly projecting flanges 25 which engage in diametrically opposed circumferential slots 26 in the shell 17.

After an injection the cap 16 is replaced on the barrel, but ultimately the needle assembly 11 has to be removed. Taking the cap off and then unscrewing the assembly exposes the handler to being pricked by the needle, which no longer has its sheath. But with this cap 16, by pressing the depressions 23 the tongues 19 flex inwardly and the wedge portions 21 engage the skirt 13 of the needle assembly. The cap and barrel are then mutually rotated and the gripped needle assembly is unscrewed. It can continue to be gripped by the cap as it is separated from the barrel, and then dropped into a sharps bin by the handler relaxing his squeeze on the over-mould.

The invention claimed is:

1. A cap for an injection device of the type which presents a needle assembly to the exterior thereof for removal after use, the cap being of two part construction with a shell of hard material having opposite inwardly flexible tongues defined by slots in the shell and an over-mould of relatively soft deformable material extending over at least the tongues and the slots, the tongues being squeezable towards each other through the over-mould to grip the needle assembly when the cap is fitted after an injection.

2. A cap according to claim 1, which is of generally elongate form, closed at one end and open at the other.

3. A cap according to claim 1, wherein the tongues are defined by generally U-shaped slots, the base of each U being positioned away from the closed end of the cap.

4. A cap according to claim 1, which is coned, narrowing towards its closed, forward end.

5. A cap according to claim 3, wherein the arms of each U converge towards each other so that the tongues widen towards the open end, following the shape of the cap.

6. A cap according to claim 1, wherein the tongues are thinner, over a substantial part of their area, than the rest of the shell, to facilitate flexure.

7. A cap according to claim 1, wherein the over-mould does not conceal the whole shell, and is mainly over just the tongues and slots, with its outer surface flush with the exposed parts of the shell.

8. A cap according to claim 1, wherein the over-mould is of rubber, with depressions forming finger grips over the ends of the tongues which are to be pressed inwards.

9. A cap according to claim 1, wherein the over-mould has a positive interlock with the shell.

10. A cap according to claim 9, wherein the interlock is achieved by inwardly projecting ribs engaging in slots in the shell.

11. A cap according to claim 10, wherein the ribs are adjacent the open end of the cap.

12. A cap according to claim 2, wherein the tongues are defined by generally U-shaped slots, the base of each U being positioned away from the closed end of the cap.

13. the cap of claim 1, wherein,
the shell further comprises diametrically opposed circumferential slots perforating an entire thickness of the shell; and
the over-mold further comprises inwardly projecting flanges engaged in the diametrically opposed circumferential slots in the shell.

14. A cap for removing a used needle assembly from an injection device, comprising:
a shell having slots and opposite inwardly flexible tongues defined by the slots,
the shell including an interior end portion shaped to accept a syringe needle sheath; and
a deformable outer skin moulded contactingly over at least the tongues and the slots of the shell,
the tongues being squeezable towards each other through pressure exerted on the outer skin, the squeezed tongues gripping a syringe needle assembly to remove the needle assembly from an injection device.

15. The cap of claim 14, wherein the outer skin is rubber and the shell is hard plastic.

16. The cap of claim 14, wherein, the tongues are defined by generally U-shaped slots, the base of each U being positioned away from a closed end of the cap.

17. The cap of claim 14, wherein,
the shell further comprises diametrically opposed circumferential slots perforating an entire thickness of the shell; and
the skin further comprises inwardly projecting flanges engaged in the diametrically opposed circumferential slots in the shell.

18. A cap for removing a used needle assembly from an injection device, comprising:
a hard shell having slots and opposite inwardly flexible tongues defined by the slots; and
a deformable outer rubber skin fitted contacting at least the tongues and over the slots of the shell,
the tongues being squeezable towards each other through pressure exerted on the outer skin, the squeezed tongues gripping a syringe needle assembly to remove the needle assembly from an injection device.

19. The cap of claim 18, wherein, the tongues are defined by generally U-shaped slots, the base of each U being positioned away from a closed end of the cap.

* * * * *